(12) United States Patent
Dams

(10) Patent No.: US 6,977,307 B2
(45) Date of Patent: Dec. 20, 2005

(54) WATER SOLUBLE OR WATER DISPERSIBLE FLUOROCHEMICAL SILANES FOR RENDERING SUBSTRATES OIL AND WATER REPELLENT

(75) Inventor: Rudolf J. Dams, Antwerp (BE)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 10/053,001

(22) Filed: Jan. 17, 2002

(65) Prior Publication Data

US 2003/0168783 A1 Sep. 11, 2003

(30) Foreign Application Priority Data

Jan. 19, 2001 (EP) .............................................. 01200208

(51) Int. Cl.[7] .............................. B05D 3/10; B05D 3/04; C07F 7/04; C07F 7/12; C04B 33/34
(52) U.S. Cl. ....................... 556/485; 427/340; 427/344; 264/602
(58) Field of Search .......................... 556/485; 427/340, 427/344; 264/602

(56) References Cited

U.S. PATENT DOCUMENTS

| | | | |
|---|---|---|---|
| 2,803,615 A | 8/1957 | Ahlbrecht et al. | |
| 4,085,137 A | 4/1978 | Mitsch et al. | |
| 4,633,004 A | 12/1986 | Boutevin et al. | |
| 4,761,459 A | 8/1988 | Matsuo et al. | |
| 4,927,950 A | 5/1990 | Hisamoto et al. | |
| 5,274,159 A | 12/1993 | Pellerite et al. | |
| 5,292,796 A | 3/1994 | Dams et al. | |
| 5,442,011 A | 8/1995 | Halling | |
| 5,453,540 A | 9/1995 | Dams et al. | |
| 5,482,991 A | 1/1996 | Kumar et al. | |
| 5,527,931 A | 6/1996 | Rich et al. | |
| 5,550,184 A | 8/1996 | Halling | |
| 5,608,003 A | 3/1997 | Zhu | |
| 5,760,126 A | 6/1998 | Engle et al. | |
| 5,980,992 A | 11/1999 | Kistner et al. | |
| 5,998,549 A | 12/1999 | Milbourn et al. | |
| 6,156,860 A | 12/2000 | Tanaka et al. | |
| RE37,022 E | 1/2001 | Sugiyama et al. | |
| 6,649,272 B2 | 11/2003 | Moore et al. | |

FOREIGN PATENT DOCUMENTS

| | | |
|---|---|---|
| EP | 0222157 | 5/1987 |
| EP | 0248383 | 12/1987 |
| EP | 0337474 | 10/1989 |
| EP | 0426530 | 5/1991 |
| EP | 0526976 | 2/1992 |
| EP | 933377 A2 | 8/1999 |
| EP | 937748 A2 | 8/1999 |
| EP | 978524 A1 | 2/2000 |
| JP | 62-63560 | 3/1987 |
| JP | 07-062997 | 8/1993 |
| JP | 2000169483 | 6/2000 |
| WO | WO 96/16630 | 6/1996 |
| WO | WO 97/00230 | 1/1997 |
| WO | WO 99/29636 | 6/1999 |

OTHER PUBLICATIONS

10/053,396, Jan. 17, 2002, Fluorochemical composition comprising a fluorochemical oligomeric silane for rendering substrates oil and water repellent.

Standard Test Number 22, published in the 1985 Technical Manual and Yearbook of the American Association of Textile Chemists and Colorists (AATCC).

Jenkins A D et al: "Glossary of Basic in Polymer Science" Pure & Applied Chemistry, Pergamon Press, Oxford, GB, vol. 68, No. 12, 1996, pp 2287–2311, XP000933983.

*Primary Examiner*—Brian J. Davis

(57) ABSTRACT

A water soluble or water dispersible fluorochemical silane represented by the general formula (I):

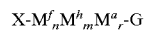

wherein X represents the residue of an initiator or hydrogen; $M^f$ represents units derived from one or more fluorinated monomer; $M^h$ represents units derived from one or more non-fluorinated monomer; $M^a$ represents units having a silyl group; G is a monovalent organic group comprising the residue of a chain transfer agent; n represents a value of 1 to 100; m represents a value of 0 to 100; and r represents a value of 0 to 100; and n+m+r is at least 2; with the proviso that at least one of the following conditions is fulfilled: (a) G contains a silyl group of the formula (III):

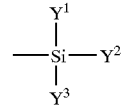

wherein $Y^1$, $Y^2$ and $Y^3$ each independently represents an alkyl group, an aryl group or a hydrolyzable group and at least one of $Y^1$, $Y^2$ and $Y^3$ represents a hydrolyzable water solubilising group; or (b) r is at least 1 and at least one of $Y^4$, $Y^5$ and $Y^6$ represents a hydrolyzable water solubilizing group.

22 Claims, No Drawings

WATER SOLUBLE OR WATER DISPERSIBLE FLUOROCHEMICAL SILANES FOR RENDERING SUBSTRATES OIL AND WATER REPELLENT

This application claims priority from EP Patent Application No. 01200208.5, filed on Jan. 19, 2001.

FIELD OF INVENTION

The present invention relates to fluorochemical silanes, in particular oligomeric fluorochemical silanes that can be dissolved or dispersed in water, and to a method of making same. The invention further relates to aqueous compositions of the fluorochemical silane and to a method of treatment of a substrate therewith.

BACKGROUND

Fluorochemical compounds are well known and commercially used to render various substrates oil- and water repellent and to provide other desirable properties thereto such as soil repellency and soil release. For example, U.S. Pat. Nos. 5,292,796 and 5,453,540 disclose certain fluorochemical oligomers for the treatment of substrates such as, for example, fibrous substrates. The oligomers disclosed are typically functionalised with an isocyanate group to cause reaction with the fibrous substrate surface.

Fluorochemical compounds including silanes are also known and commercially available. For example, FC 405 is a fluorochemical silane that is commercially available from 3M Company for rendering substrates such as glass or ceramics oil and water repellent. However, this product is solvent based and it would be desirable to have water based product for treating such substrates as glass or ceramics.

U.S. Pat. No. 5,980,992 discloses the use of fluorochemical silanes for the treatment of silicon-containing organic polymeric surfaces to restore the repellency thereof. The repellency of silicon-containing organic polymeric surfaces that become spent during use can be restored by treatment with fluorinated silane containing compositions. These compositions are however applied from solvent.

Fluorochemical compounds that can be applied from water are also known in the art. For example, U.S. Pat. No. 5,274,159 discloses a fluorochemical silane having hydrolysable polyoxyalkylene groups bonded to the silicone atom of the silyl groups. These groups are taught to hydrolyse in the presence of an acid or base catalyst after application to a substrate. However, the obtained oil- and water-repellency properties of the coated substrate and abrasion resistance leave room for further improvement.

Still further aqueous based fluorochemical compositions are disclosed in U.S. Pat. No. 5,550,184 and WO 99/29636. U.S. Pat. No. 5,550,184 discloses a hydrolysed silane emulsion obtained by emulsifying a hydrolysable perfluoroalkoxysilane in water in the presence of an emulsifier. WO 99/29636 discloses aqueous emulsions containing 1) a fluorocarbon silane hydrolysate generated in the presence of a surfactant and 2) a silicate, which provides a clear and smooth coated surface having water repellency and heat resistance when applied to a substrate.

Despite the many known fluorochemical compositions for the treatment of surfaces, there continues to be a desire to find further beneficial fluorochemical compositions and in particular fluorochemical compositions for the treatment of hard surfaces that can be applied in an environmental friendly way from an aqueous based composition. Preferably, such fluorochemical composition will have a high water repellency, high oil repellency and preferably have a high durability. Further desired properties are good stain resistance and/or stain release. Desirably, the compositions are easy to manufacture in a cost effective and convenient way.

SUMMARY

The present invention provides new fluorochemical silanes, compositions containing such silanes, methods of using such silanes, and methods for making such silanes.

The present invention provides a water soluble or water dispersible fluorochemical silane represented by the general formula:

$$X\text{-}M^f_n M^h_m M^a_r\text{-}G \qquad (I)$$

wherein X represents the residue of an initiator or hydrogen;
$M^f$ represents units derived from one or more fluorinated monomer;
$M^h$ represents units derived from one or more non-fluorinated monomer;
$M^a$ represents units having a silyl group represented by the formula:

$$\begin{array}{c} Y^4 \\ | \\ -\!\!\!-\mathrm{Si}\!-\!\!\!-Y^5 \\ | \\ Y^6 \end{array} \qquad (II)$$

wherein each of $Y^4, Y^5$ and $Y^6$ independently represents an alkyl group, an aryl group or a hydrolyzable group;

G is a monovalent organic group comprising the residue of a chain transfer agent;
n represents a value of 1 to 100;
n represents a value of 1 to 100;
and r represents a value of 0 to 100;
and n+m+r is at least 2;

with the proviso that at least one of the following conditions is fulfilled: (a) G contains a silyl group of the formula:

$$\begin{array}{c} Y^1 \\ | \\ -\!\!\!-\mathrm{Si}\!-\!\!\!-Y^2 \\ | \\ Y^3 \end{array} \qquad (III)$$

wherein $Y^1$, $Y^2$ and $Y^3$ each independently represents an alkyl group, an aryl group or a hydrolyzable group and at least one of $Y^1$, $Y^2$ and $Y^3$ represents a hydrolyzable water solubilising group; or
(b) r is at least 1 and at least one of $Y^4$, $Y^5$ and $Y^6$ represents a hydrolyzable water solubilizing group.

The fluorochemical silane of the invention can be dissolved or dispersed in water and accordingly, aqueous compositions can be prepared therefrom allowing environmental friendly application of the fluorochemical silane. Additionally, the fluorochemical silane of the invention can impart good oil- and water repellency properties when applied to a substrate and in particular when applied to hard surfaces. Good stain resistance and stain release may also be obtained. Finally, the fluorochemical silane when applied to a substrate can impart durable oil- and water repellency properties.

The present invention further provides aqueous compositions including the fluorochemical silane, a method for making the above fluorochemical silane, and method of treatment of a substrate with the fluorochemical silane. By the term "aqueous composition" in connection with the present invention is generally meant that a major amount of the composition consists of water, i.e. the composition contains at least 51% by weight of water, preferably at least 80% by weight of water.

DETAILED DESCRIPTION OF ILLUSTRATIVE EMBODIMENTS

The water soluble or water dispersible fluorochemical silanes of this invention, corresponding to the general formula I, are generally oligomers that can be prepared by free-radical oligomerization of a fluorochemical monomer and optionally a non-fluorinated monomer in the presence of a chain transfer agent. The oligomers should also include one or more silyl groups that have one or more hydrolyzable water solubilising groups. By the term "water solubilising groups" is meant that these groups help solubilising or dispersing the fluorochemical silane in water. These water solubilising groups should also be hydrolyzable under appropriate conditions so that, upon application of the fluorochemical silane to a substrate, these water solubilising groups can be removed from the coating so that such coating can display the desired oil and water repellent properties. The silyl groups having one or more hydrolysable water solubilising groups can be included in the fluorochemical silane by copolymerising the fluorochemical monomer with a silyl group-containing monomer or through the use of chain transfer agent that includes a silyl group. Alternatively, a functionalised chain transfer agent or functionalised comonomer can be used which can be reacted with a silyl group containing reagent subsequent to the oligomerization. When a silyl group containing monomer or chain transfer agent is used during the free radical oligomerization, such silyl group need not contain the water solubilising groups. Upon oligomerization, the oligomer may be further reacted with a reactant including a water solubilising group to introduce such groups on the silyl moieties contained in the oligomer.

The total number of units in the oligomer is represented by the sum of n, m and r and is generally at least 2 and preferably at least 3 so as to render the compound oligomeric. The value of n in the fluorochemical oligomer is typically between 1 and 100 and preferably between 2 and 20. The values of m and r are typically between 0 and 100 and preferably between 1 and 30. According to a preferred embodiment, the value of m is less than that of n and n+m+r is at least 2. The molecular weight of the fluorochemical oligomers is typically between about 400 and 100000, preferably between 800 and 20000.

The fluorochemical silane of the present invention comprises at least one hydrolyzable water solubilizing group, in order to render the oligomer water soluble or water dispersible. By the term "water soluble" is meant that a concentration of at least 0.1% by weight, preferably 0.5% by weight, of the fluorochemical silane can be dissolved in water at ambient temperature. By the term "water dispersible" is meant that a dispersion of at least 0.1% by weight of the fluorochemical silane in water can be made that is stable for at least 1 hour, preferably for at least 4 hours, without additional emulsifier present. The fluorochemical silane of the present invention preferably contains at least 20% (based on total weight of the silane), more preferably at least 30% by weight, most preferably at least 40% by weight of hydrolysable water solubilizing groups.

The hydrolyzable water solubilizing groups of the fluorochemical silane can be ionic or non-ionic. Typical examples of a hydrolyzable water solubilizing group that are non-ionic include poly(oxyalkylene) groups. An oxyalkylene unit in the poly(oxyalkylene) group preferably has 2 or 3 carbon atoms, such as $-OCH_2-CH_2-$, $-OCH_2-CH_2-CH_2-$, and $-OCH(CH_3)CH_2-$, the oxyalkylene units in the poly(oxyalkylene) group can be the same, as in poly(oxyethylene), or present as a mixture, as in straight or branched chain or randomly distributed oxyethylene and oxypropylene units or as in a straight or branched chain of blocks of oxyethylene units and blocks of oxypropylene units, as long as the poly(oxyalkylene)group remains water soluble or water dispersible. Particularly preferred poly(oxyalkylene) groups are polyoxyethylene and alkoxypolyoxyethylenes that have a molecular weight up to about 1500. Preferably, the number of oxyalkylene units in a poly(oxyalkylene) is between 2 and 120 and more preferably between 2 and 48.

Illustrative examples of ionic hydrolysable water solubilizing groups useful herein include anionic, cationic and zwitterionic groups. Specific examples of ionic hydrolysable water solubilizing groups include $-OCH_2CH_2N^+(CH_3)_3I^-$, $-OCH_2CH_2N^+(CH_3)_2CH_2CH_2CH_2SO_3^-$ and $-OCH_2CH_2N^+(CH_3)_3Cl^-$.

It will further be appreciated by one skilled in the art that the preparation of water soluble or water dispersible fluorochemical silanes according to the present invention results in a mixture of compounds and accordingly, the general formula (I) should be understood as representing a mixture of compounds whereby the indices n, m and r in formula I represent the molar amount of the corresponding unit in the mixture. Accordingly, it will be clear that n, m and r can be fractional values.

The units $M^f$ of the fluorochemical silane are generally derived from fluorochemical monomers corresponding to the formula:

$$R_f\text{-}Q\text{-}E^1 \qquad (IV)$$

wherein $R^f$ represents a fluoroaliphatic group containing at least 3 carbon atoms or a fluorinated polyether group. Q represents an organic divalent linking group and $E^1$ represents a free radical polymerizable group.

The fluoroaliphatic group $R_f$, in the fluorochemical monomer, is a fluorinated, stable, inert, preferably saturated, non-polar, monovalent aliphatic radical. It can be straight chain, branched chain, or cyclic or combinations thereof. It can contain heteroatoms such as oxygen, divalent or hexavalent sulfur, or nitrogen. $R_f$ is preferably a fully-fluorinated radical, but hydrogen or chlorine atoms can be present as substituents if not more than one atom of either is present for every two carbon atoms. The $R_f$ radical typically has at least 3 and up to 18 carbon atoms, preferably 3 to 14, especially 4 to 10 carbon atoms, and preferably contains about 40% to about 80% fluorine by weight, more preferably about 50% to about 78% fluorine by weight. The terminal portion of the $R_f$ radical is a perfluorinated moiety, which will preferably contain at least 7 fluorine atoms, e.g., $CF_3CF_2CF_2-$, $(CF_3)_2CF-$, $F_5SCF_2-$. The preferred $R_f$ radicals are fully or substantially fluorinated and are preferably those perfluorinated aliphatic radicals of the formula $C_nF_{2n+1}-$ where n is 3 to 18, particularly 4 to 10.

The $R_f$ group can also be a perfluoropolyether group. The perfluoropolyether group $R_f$ can include linear, branched, and/or cyclic structures, that may be saturated or unsaturated, and substituted with one or more oxygen atoms.

It is preferably a perfluorinated group (i.e., all C—H bonds are replaced by C—F bonds). More preferably, it includes perfluorinated repeating units selected from the group of —$(C_nF_{2n})$—, —$(C_nF_{2n}O)$—, —$(CF(Z))$—, —$(CF(Z)O)$—, —$(CF(Z)C_nF_{2n}O)$—, —$(C_nF_{2n}CF(Z)O)$—, —$(CF_2CF(Z)O)$—, and combinations thereof. In these repeating units Z is a perfluoroalkyl group, an oxygen-substituted perfluoroalkyl group, a perfluoroalkoxy group, or an oxygen-substituted perfluoroalkoxy group, all of which can be linear, branched, or cyclic, and preferably have about 1 to about 9 carbon atoms and 0 to about 4 oxygen atoms. The terminal groups can be $(C_nF_{2n+1})$—, $(C_nF_{2n+1}O)$— or $(X'C_nF_{2n}O)$—, wherein X' is H, Cl, or Br, for example. Preferably, these terminal groups are perfluorinated. In these repeating units or terminal groups, n is 1 or more, and preferably about 1 to about 4. Particularly preferred approximate average structures for a perfluoropolyether group include $C_3F_7O(CF(CF_3)CF_2O)_pCF(CF_3)$— and $CF_3O(C_2F_4O)_pCF_2$— wherein an average value for p is 1 to about 50. As synthesized, these compounds typically include a mixture of polymers. The approximate average structure is the proximate average of the mixture of polymers.

Difunctional fluorochemical monomers can also be used provided the resulting fluorochemical silane remains water soluble or dispersible at least at 0.1% by weight. Accordingly, $M^f$ in formula I can further be derived from a difunctional fluorochemical monomer corresponding to the formula:

$$E^a\text{-}Q^a\text{-}R^1{}_f\text{-}Q^b\text{-}E^b \qquad (V)$$

wherein $Q^a$ and $Q^b$ each independently represents an organic divalent linking group and $E^a$ and $E^b$ each independently represent a free radical polymerizable group. $R^1{}_f$ represents a divalent perfluoropolyether group such as, for example, —$(CF(CF_3)CF_2O)_p$—, —$(CF_2O)_p(CF_2CF_2O)_q$—, —$CF(CF_3)(CF_2CF(CF_3)O)_pCF(CF_3)O$—, —$(CF_2O)_p(CF_2CF_2O)_qCF_2$—, —$(CF_2CF_2O)_p$—, —$(CF_2CF_2CF_2O)_p$—, wherein an average value for p and q is 1 to about 50. The molecular weight of the difunctional fluorochemical monomer should generally be between about 200 and 1000, more preferably between 300 and 600.

The linking groups Q, $Q^a$ and $Q^b$ in the above formulas (IV) and (V) link the fluoroaliphatic or the fluorinated polyether group $R_f$ or $R^1{}_f$ to the free radical polymerizable group $E^1$, $E^a$ or $E^b$ and are generally non-fluorinated organic linking groups. The linking groups preferably contain from 1 to about 20 carbon atoms and may optionally contain oxygen, nitrogen, or sulfur-containing groups or a combination thereof. The linking groups are preferably free of functional groups that substantially interfere with free-radical oligomerization (e.g., polymerizable olefinic double bonds, thiols, and other such functionality known to those skilled in the art). Illustrative examples of suitable linking groups Q include straight chain, branched chain or cyclic alkylene, arylene, aralkylene, oxy, oxo, hydroxy, thio, sulfonyl, sulfoxy, amino, imino, sulfonamido, carboxamido, carbonyloxy, urethanylene, ureylene, and combinations thereof such as sulfonamidoalkylene. Preferred linking groups are selected from the group consisting of alkylene and an organic divalent linking group according to the following formulae:

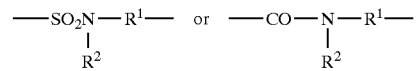

wherein $R^1$ represents a hydrogen or a linear or branched alkylene having 2 to 4 carbon atoms and $R^2$ represents a hydrogen or an alkyl having 1 to 4 carbon atoms. $E^1$, $E^a$ and $E^b$ are a free radically polymerizable groups that typically contain an ethylenically unsaturated group capable of undergoing a free radical polymerization. Suitable groups include, for example, moieties derived from vinyl ethers, vinyl esters, allyl esters, vinyl ketones, styrene, vinyl amide, acrylamides, maleates, fumarates, acrylates and methacrylates. Of these, the esters of alpha, beta unsaturated acids, such as the acrylates and methacrylates are preferred.

Fluorochemical monomers $R_f\text{-}Q\text{-}E^1$ as described above and methods for the preparation thereof are known and disclosed, e.g., in U.S. Pat. No. 2,803,615. Illustrative examples of such compounds include general classes of fluorochemical acrylates, methacrylates, vinyl ethers, and allyl compounds containing fluorinated sulfonamido groups, acrylates or methacrylates derived from fluorochemical telomer alcohols, acrylates or methacrylates derived from fluorochemical carboxylic acids, and perfluoroalkyl acrylates or methacrylates as disclosed in EP-A-526 976. Fluorinated polyetheracrylates or methacrylates suitable for use herein are described in U.S. Pat. No. 4,085,137.

Preferred examples of fluorochemical monomers include:

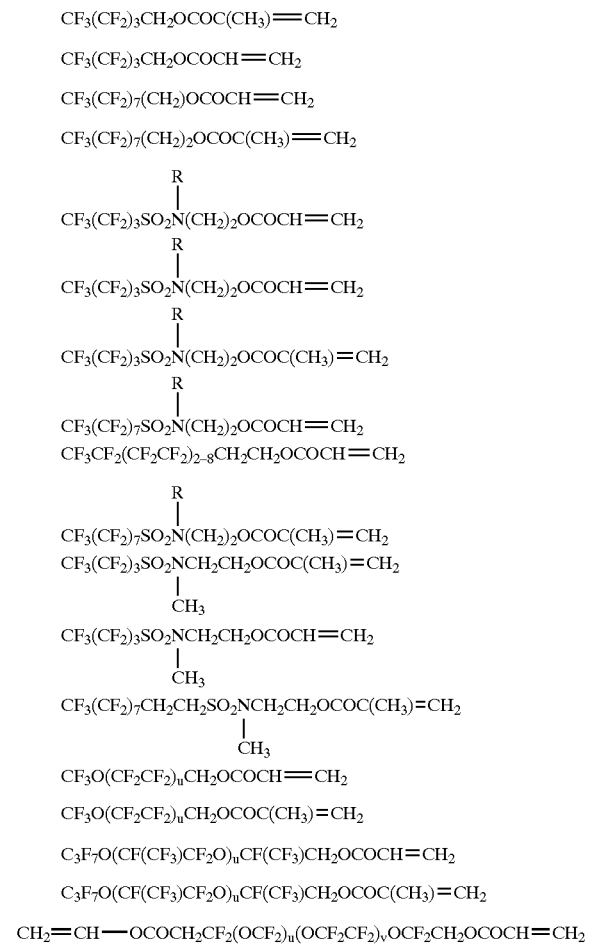

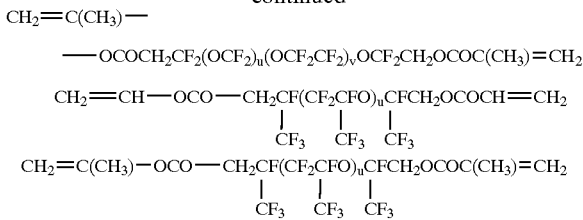

wherein R represents methyl, ethyl or n-butyl and u and v are about 1 to 50.

The units $M^h$ of the fluorochemical silane (when present) are generally derived from a non-fluorinated monomer, preferably a monomer consisting of a polymerizable group and a hydrocarbon moiety. Hydrocarbon group containing monomers are well known and generally commercially available. Illustrative examples of non-fluorinated monomers from which units $M^h$ can be derived include general classes of ethylenic compounds capable of free-radical polymerization, such as, for example, allyl esters such as allyl acetate and allyl heptanoate; alkyl vinyl ethers or alkyl allyl ethers such as cetyl vinyl ether, dodecylvinyl ether, 2-chloroethylvinyl ether, ethylvinyl ether; unsaturated acids such as acrylic acid, methacrylic acid, alpha-chloro acrylic acid, crotonic acid, maleic acid, fumaric acid, itaconic acid and their anhydrides and their esters such as vinyl, allyl, methyl, butyl, isobutyl, hexyl, heptyl, 2-ethylhexyl, cyclohexyl, lauryl, stearyl, isobornyl or alkoxy ethyl acrylates and methacrylates; alpha-beta unsaturated nitriles such as acrylonitrile, methacrylonitrile, 2-chloroacrylonitrile, 2-cyanoethyl acrylate, alkyl cyanoacrylates; alpha,beta-unsaturated carboxylic acid derivatives such as allyl alcohol, allyl glycolate, acrylamide, methacrylamide, n-diisopropyl acrylamide, diacetoneacrylamide, N,N-diethylaminoethylmethacrylate, N-t-butylamino ethyl methacrylate; styrene and its derivatives such as vinyltoluene, alpha-methylstyrene, alpha-cyanomethyl styrene; lower olefinic hydrocarbons which can contain halogen such as ethylene, propylene, isobutene, 3-chloro-1-isobutene, butadiene, isoprene, chloro and dichlorobutadiene and 2,5-dimethyl-1,5-hexadiene, and allyl or vinyl halides such as vinyl and vinylidene chloride. Preferred non-fluorinated monomers include hydrocarbon group containing monomers such as those selected from octadecylmethacrylate, laurylmethacrylate, butylacrylate, N-methylol acrylamide, isobutylmethacrylate, ethylhexyl acrylate and ethylhexyl methacrylate; and vinylcloride and vinylidene chloride.

The fluorochemical silane of the invention may further include units $M^a$ which are derivable from a monomer represented by the formula:

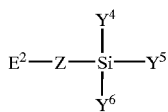 (VI)

wherein each of $Y^4$, $Y^5$ and $Y^6$ independently represents an alkyl group, an aryl group, a hydrolysable group including hydrolyzable water solubilizing group as well as other hydrolyzable groups that are not water solubilizing; Z represents an organic divalent linking group and $E^2$ represents a free radical polymerizable group such as for example listed above with respect to $E^1$. By the term "derivable from" is meant that the units $M^a$ derive directly from the free radical polymerization of the monomers according to formula (VI) as well as indirectly by further reaction of the silyl groups included in the oligomer upon polymerization of monomers according to formula (VI). In particular, as will be described in more detail below, a water solubilising group may be introduced into the fluorochemical silane after a polymerization or oligomerization involving a monomer according to formula (VI) by reacting the resulting silyl group with a compound that includes a water solubilising group and that can displace a substituent on the silicone atom.

The organic divalent linking group Z preferably contains from 1 to about 20 carbon atoms. Z can optionally contain oxygen, nitrogen, or sulfur-containing groups or a combination thereof, and Z is preferably free of functional groups that substantially interfere with free-radical oligomerization (e.g., polymerizable olefinic double bonds, thiols, and other such functionality known to those skilled in the art). Illustrative examples of suitable linking groups Z include straight chain, branched chain or cyclic alkylene, arylene, aralkylene, oxyalkylene, carbonyloxyalkylene, oxycarboxyalkylene, carboxyamidoalkylene, urethanylenealkylene, ureylenealkylene and combinations thereof. Preferred linking groups are selected from the group consisting of alkylene, oxyalkylene and carbonyloxyalkylene.

$Y^4$, $Y^5$, and $Y^6$ independently represents an alkyl group, an aryl group, a hydrolysable group or a hydrolyzable water solubilizing group. Typical examples of hydrolyzable groups include halogen, alkoxy, acyloxy, acyl or aryloxy groups. Hydrolysable water solubilizing groups are as disclosed above.

Monomers according to formula VI that include a hydrolysable water solubilising group can conveniently be prepared starting from monomers represented by formula VII

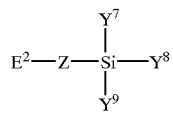 VII wherein each of $Y^7$, $Y^8$ and $Y^9$ independently represents an alkyl group, an aryl group or a hydrolyzable group, selected from halogen, alkoxy groups, acyloxy groups, acyl groups and aryloxy groups with the proviso that at least one of $Y^7$, $Y^8$ and $Y^9$ represent a hydrolyzable group. Z and $E^2$ are as defined above. The monomers of formula VII can be reacted with poly(oxyalkylene) group containing compounds capable of displacing a hydrolyzable group in the monomer of formula VII. Illustrative examples of monomers according to formula VII include vinyltrichlorosilane, vinyltrimethoxysilane, vinyltriethoxysilane and alkoxysilane functionalised acrylates or methacrylates, such as methacryloyloxypropyl trimethoxysilane. The monomers of formula VI can conveniently be prepared by exchange reaction of the hydrolyzable group, preferably alkoxy or aryloxy, in compounds of formula VII with a hydrolyzable water solubilizing group, such as e.g. a poly(oxyalkylene) group. Typical examples of poly(oxyalkylene) group containing compounds include alkyl ethers of polyglycols such as e.g. methyl or ethyl ether of polyethyleneglycol, hydroxy terminated methyl or ethyl ether of a random or block copolymer of ethyleneoxide and propyleneoxide, amino terminated methyl or ethyl ether of polyethyleneoxide. Suitable examples include methoxydiethyleneglycol, methoxytriethyleneglycol, Carbowax™ 350, Carbowax™

550 and Carbowax™ 750. The hydrolyzable group exchange reaction is conveniently carried out neat, in the presence of an inhibitor, such as methyl ethyl hydroquinone (MEHQ) or phenothiazine in order to prevent polymerization of the monomer. The reaction can be done at a temperature between 60° C. and 200° C., preferably 80° C. to 180° C., during 5 to 8 hours. Ionic hydrolyzable water solubilizing groups can be introduced by reacting the compounds of formula VII with an alcohol or amine that is functionalised with a ionic group. Illustrative examples thereof include $HOCH_2CH_2N^+(CH_3)_3I^-$, $HOCH_2CH_2N^+(CH_3)_2CH_2CH_2CH_2SO_3^-$ and $HOCH_2CH_2N^+(CH_3)_3Cl^-$.

The fluorochemical silane is conveniently prepared through a free radical polymerization of a fluorinated monomer with optionally a non-fluorinated monomer and a monomer containing a silyl group in the presence of a chain transfer agent. A free radical initiator is generally used to initiate the polymerization or oligomerization reaction. Commonly known free-radical initiators can be used and examples thereof include azo compounds, such as azobisisobutyronitrile (ABIN), azo-2-cyanovaleric acid and the like, hydroperoxides such as cumene, t-butyl and t-amyl hydroperoxide, dialkyl peroxides such as di-t-butyl and dicumylperoxide, peroxyesters such as t-butylperbenzoate and di-t-butylperoxy phthalate, diacylperoxides such as benzoyl peroxide and lauroyl peroxide.

The oligomerization reaction can be carried out in any solvent suitable for organic free-radical reactions. The reactants can be present in the solvent at any suitable concentration, e.g., from about 5 percent to about 90 percent by weight based on the total weight of the reaction mixture. Illustrative examples of suitable solvents include aliphatic and alicyclic hydrocarbons (e.g., hexane, heptane, cyclohexane), aromatic solvents (e.g., benzene, toluene, xylene), ethers (e.g., diethylether, glyme, diglyme, diisopropyl ether), esters (e.g., ethyl acetate, butyl acetate), alcohols (e.g., ethanol, isopropyl alcohol), ketones (e.g., acetone, methylethyl ketone, methyl isobutyl ketone), sulfoxides (e.g., dimethyl sulfoxide), amides (e.g., N,N-dimethylformamide, N,N-dimethylacetamide), halogenated solvents such as methylchloroform, FREON™ 113, trichloroethylene, α,α,α-trifluorotoluene, and the like, and mixtures thereof.

The oligomerization reaction can be carried out at any temperature suitable for conducting an organic free-radical reaction. Particular temperature and solvents for use can be easily selected by those skilled in the art based on considerations such as the solubility of reagents, the temperature required for the use of a particular initiator, molecular weight desired and the like. While it is not practical to enumerate a particular temperature suitable for all initiators and all solvents, generally suitable temperatures are between about 30° C. and about 200° C.

The fluorochemical oligomer is prepared in the presence of chain transfer agent. Suitable chain transfer agents typically include a hydroxy-, amino-, or mercapto group. The chain transfer agent may include two or more of such hydroxy, amino- or mercapto groups. Illustrative examples of chain transfer agents useful in the preparation of the fluorochemical oligomer include those selected from 2-mercaptoethanol, 3-mercapto-2-butanol, 3-mercapto-2-propanol, 3-mercapto-1-propanol, 3-mercapto-1,2-propanediol, 2-mercapto-ethylamine, di(2-mercaptoethyl)sulfide, octylmercaptane and dodecylmercaptane.

In a preferred embodiment a chain transfer agent containing a silyl group having one or more hydrolyzable groups is used in the oligomerization to produce the fluorochemical oligomer. Transfer agents including a silyl group include those according to formula VIII.

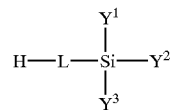

VIII wherein $Y^1$, $Y^2$ and $Y^3$ each independently represents an alkyl group, preferably a $C_1$–$C_8$ alkyl group such as methyl, ethyl or propyl or an alkyl group containing a cycloalkyl such as cyclohexyl or cylcopentyl, an aryl group such as phenyl, an alkylaryl group or an aralkyl group, a hydrolysable group such as for example halogen, alkoxy groups such as methoxy or ethoxy, acyloxy groups, acyl groups or aryloxy groups or a hydrolysable water solubilizing group, such as a poly(oxyalkylene) group, with at least one of $Y^1$, $Y^2$ and $Y^3$ representing a hydrolysable group. L represents a divalent linking group such as —O—, —S— and —NR wherein R represents an alkyl or aryl group.

Preferred chain transfer agents are those in which L represents —S-$Q^1$- with $Q^1$ being linked to the silicone atom in formula VIII and wherein $Q^1$ represents an organic divalent linking group such as for example a straight chain, branched chain or cyclic alkylene, arylene or aralkylene.

A single chain transfer agent or a mixture of different chain transfer agents may be used. The preferred chain transfer agents are 2-mercaptoethanol, octylmercaptane and 3-mercaptopropyltrimethoxysilane. A chain transfer agent is typically present in an amount sufficient to control the number of polymerized monomer units in the oligomer and to obtain the desired molecular weight of the oligomeric fluorochemical silane. The chain transfer agent is generally used in an amount of about 0.05 to about 0.5 equivalents, preferably about 0.25 equivalents, per equivalent of monomer including fluorinated and non-fluorinated monomers.

The fluorochemical silane of the present invention contains one or more hydrolyzable water solubilising groups. These hydrolysable water solubilising groups may be introduced in the fluorochemical silane by oligomerising in the presence of a chain transfer agent having a silyl group containing one or more hydrolysable water solubilising groups, for example a chain transfer agent according to formula VIII above wherein at least one of $Y^1$, $Y^2$ and $Y^3$ represents a hydrolysable water solubilising group and/or by co-oligomerising with a monomer containing a silyl group having one or more hydrolysable water solubilising groups such as a monomer according to formula VII above wherein at least one of $Y^7$, $Y^8$ and $Y^9$ represents a hydrolysable water solubilising group. According to a more preferred embodiment, a silyl group containing one or more hydrolysable water solubilising groups is formed subsequent to the oligomerization or polymerization.

According to a first embodiment for introducing a silyl group containing one or more hydrolysable water solubilising groups subsequent to the oligomerization, a fluorochemical silane is first prepared by oligomerizing fluorinated monomer and optional non-fluorinated monomer with one or more monomers according to formula VII above wherein at least one of $Y^7$, $Y^8$ and $Y^9$ represents a hydrolysable group selected from an alkoxy group, an acyloxy group, an acyl group, an aryloxy group and a halogen such as chlorine in the presence of a chain transfer agent which may optionally also contain a silyl group such as for example a chain transfer agent according to formula VIII above wherein at least one of $Y^1$, $Y^2$ and $Y^3$ represents a hydrolysable group selected from an alkoxy group, an acyloxy group, an acyl group, an aryloxy group and a halogen such as chlorine. Subsequent to the oligomerization, at least part of the hydrolysable groups are exchanged by hydrolysable water solubilising groups by reacting the fluorochemical silane with a compound containing the water solubilising groups and capable of displacing the hydrolysable groups of the silyl moieties in the fluorochemical silane. Illustrative examples of such compounds include in particular hydroxy or amino terminated polyoxyalkylene compounds such as for example alkyl ethers of polyglycols such as, e.g., methyl or ethyl ether of polyethyleneglycol, hydroxy terminated methyl or ethyl ether of a random or block copolymer of ethyleneoxide and propyleneoxide, amino terminated methyl or ethyl ether of polyethyleneoxide. Specific examples include methoxydiethyleneglycol, methoxytriethyleneglycol, Carbowax™ 350, Carbowax™ 550 and Carbowax™ 750. Alcohols or amines functionalised with an ionic group as mentioned above can be used to introduce ionic hydrolysable water solubilising groups.

The exchange reaction is conveniently carried out immediately after the oligomerisation reaction, at a temperature between 60° C. and 200° C., preferably 80° C. to 180° C., during 5 to 8 hours, while stripping off solvent and products formed as a result of the exchange reaction such as alcohol. Optionally a catalyst, such as paratoluene sulphonic acid, can be used. It is to be appreciated that the exchange reaction may be incomplete and reaction product may comprise mixtures of compounds.

As a variation to the above method for introducing the hydrolysable water solubilising groups, the oligomerization may be carried out without the use of the silyl group containing monomer but with a chain transfer agent containing a silyl group. Upon the oligomerization, the hydrolyzable water solubilising groups may then again be introduced through the exchange reaction described above.

A further embodiment for producing the fluorochemical silane, involves the polymerisation or oligomerisation of one or more fluorinated monomers and a monomer having a functional group available for subsequent reaction such as for example a hydroxy group or amino group in the presence of a chain transfer agent. Examples of such monomers include hydroxy or amino functionalised acrylate or methacrylates, such as 2-hydroxyethyl(meth)acrylate, 3-hydroxypropyl(meth)acrylate, 6-hydroxyhexyl(meth) acrylate and the like. Alternative to or in addition to the use of functionalised monomer, a functionalised chain transfer agent can be used. For example, a chain transfer agent can be used that is functionalised with a group such as a hydroxy group or an amino group. Illustrative examples of such chain transfer agents include 2-mercaptoethanol, 3-mercapto-2-butanol, 3-mercapto-2-propanol, 3-mercapto-1-propanol, 3-mercapto-1,2-propanediol and 2-mercapto-ethylamine. Subsequent to the oligomerisation the functional group contained in the comonomer and/or chain transfer agent can be reacted with a compound including a silyl group having hydrolysable groups and that is capable of reacting with the functional group contained in the comonomer and/or chain transfer agent.

Suitable compounds for reacting with the functional groups included in the monomer or chain transfer agent include compounds according to the following formula:

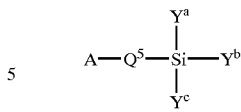

IX wherein A represents a functional group capable of undergoing a condensation reaction with the functional group contained in the monomer or chain transfer agent, in particular a functional group capable of condensing with a hydroxy or amino functional oligomer. Examples of A include an isocyanate or an epoxy group. $Q^5$ represents an organic divalent linking group, $Y^a$, $Y^b$ and $Y^c$ each independently represents an alkyl group, preferably a $C_1$–$C_8$ alkyl group such as methyl, ethyl or propyl or an alkyl group containing a cycloalkyl such as cyclohexyl or cylcopentyl, an aryl group such as phenyl, an alkylaryl group or an aralkyl group or hydrolysable group such as for example halogen, an alkoxy group such as methoxy or ethoxy, an acyloxy group, an acyl group or an aryloxy group and at least one of $Y^a$, $Y^b$ and $Y^c$ represents a hydrolysable group. Illustrative examples of organic divalent linking groups $Q^5$ include straight chain, branched chain or cyclic alkylene, arylene, aralkylene, oxyalkylene, carbonyloxyalkylene, oxycarboxyalkylene, carboxyamidoalkylene, urethanylenealkylene, ureylenealkylene and combinations thereof. Preferred linking groups are selected from the group consisting of alkylene, oxyalkylene and carbonyloxyalkylene.

Illustrative examples of compounds according to formula IX include 3-isocyanatopropyltrimethoxysilane and 3-epoxypropyltrimethoxysilane.

The condensation reaction is carried out under conventional conditions well-known to those skilled in the art. Preferably the reaction is run in the presence of a catalyst. Illustrative examples of suitable catalysts include tin salts such as dibutyltin dilaurate, stannous octanoate, stannous oleate, tin dibutyldi-(2-ethyl hexanoate), stannous chloride; and others known to those skilled in the art. The amount of catalyst present will depend on the particular reaction, and thus it is not practical to recite particular preferred concentrations. Generally, however, suitable catalyst concentrations are from about 0.001 percent to about 10 percent, preferably about 0.1 percent to about 5 percent, by weight based on the total weight of the reactants.

The condensation reaction is preferably carried out under dry conditions in a polar solvent such as ethyl acetate, acetone, methyl isobutyl ketone, toluene and the like. Suitable reaction temperatures will be easily determined by those skilled in the art based on the particular reagents, solvents, and catalysts being used. Suitable temperatures are typically between about room temperature and about 120 deg. C.

Subsequent to the condensation reaction with a compound according to formula IX, one or more of the hydrolysable groups in the silyl groups on the oligomer are exchanged with a hydrolysable water solubilising group in an exchange reaction as described above.

In case a functionalised chain transfer agent as set forth above is used in the oligomerization, the condensation reaction of the oligomer with a compound according to formula IX wherein A is an isocyanate group and the further exchange reaction generally results in fluorochemical silane oligomers that have an organic residue G (formula I) which can be represented by formula X:

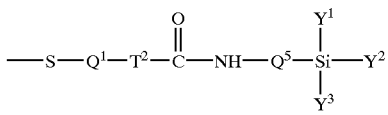

$$\text{—S—Q}^1\text{—T}^2\text{—C(=O)—NH—Q}^5\text{—Si(Y}^1\text{)(Y}^2\text{)(Y}^3\text{)} \qquad \text{X}$$

wherein $Q^1$ and $Q^5$ each independently represents an organic divalent linking group, $T^2$ represents O or NR with R being a hydrogen or an aryl or a $C_1$–$C_4$ alkyl group, $Y^1$, $Y^2$ and $Y^3$ are as defined above and at least one of $Y^1$, $Y^2$ and $Y^3$ represents a hydrolysable water solubilising group.

When a compound according to formula IX wherein A is an epoxy group is used, the organic residue may be represented by a residue according to formula XI or XII or a mixture thereof:

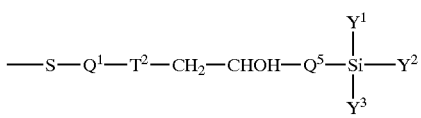

$$\text{—S—Q}^1\text{—T}^2\text{—CH}_2\text{—CHOH—Q}^5\text{—Si(Y}^1\text{)(Y}^2\text{)(Y}^3\text{)} \qquad \text{XI}$$

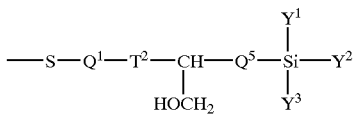

$$\text{—S—Q}^1\text{—T}^2\text{—CH(HOCH}_2\text{)—Q}^5\text{—Si(Y}^1\text{)(Y}^2\text{)(Y}^3\text{)} \qquad \text{XII}$$

wherein $Q^1$, $Q^5$, $T^2$ and $Y^1$, $Y^2$ and $Y^3$ have the meaning as defined above in formula X.

After preparation of the fluorochemical silane according to any of the methods described above, the fluorochemical silane may be isolated by evaporating any solvents used in the preparation. A solution or dispersion in water can be made by vigorously stirring the fluorochemical silane in water at neutral pH, typically at a temperature between 20 and 70° C., preferably between 30 and 50° C. and during a time sufficient to dissolve or disperse the product. The aqueous solutions or dispersions prepared typically have a stability of at least 1 hour, preferably at least 4 hours, more preferably at least 24 hours. Additional emulsifiers can be used to increase the dispersion stability, but are generally avoided in order not to obtain a substrate with optimal repellency properties, in particular water repellency. Other components, such as silica or $TiO_2$, can be present, as well as other aqueous water extenders known to those skilled in the art. Illustrative examples include silicones, siloxanes, melamines, urethanes and the like.

The hydrolysable fluorochemical silane can be used to treat substrates so as to render these oil and water repellent and/or to provide stain repellency to such substrates. Suitable substrates that can be treated in a particularly effective way with the water soluble or dispersible fluorochemical silanes of this invention include substrates having a hard surface that preferably has groups capable of reacting with the fluorochemical silane according to formula (I). Preferably, such reactivity of the surface of the substrate is provided by active hydrogen atoms. When such active hydrogen atoms are not present, the substrate may first be treated in a plasma containing oxygen or in a corona atmosphere to make them reactive to the fluorochemical silane. Particularly preferred substrates include ceramics, glass, metal, natural and man-made stone, thermoplastic materials (such as poly(meth)acrylate, polycarbonate, polystyrene, styrene copolymers, such as styrene acrylonitrile copolymers, polyesters, polyethylene terephtalate), paints (such as those on acrylic resins), powder coatings (such as polyurethane or hybrid powder coatings), and wood. Various articles can be effectively treated with the fluorochemical silane solution of the present invention to provide a water and oil repellent coating thereon. Examples include ceramic tiles, bathtubs or toilet pots, glass shower panels, construction glass, various parts of a vehicle (such as the mirror or windscreen), glass, ceramic or enamel pottery materials.

Treatment of the substrates results in rendering the treated surfaces less retentive of soil and more readily cleanable due to the oil and water repellent nature of the treated surfaces. These desirable properties are maintained despite extended exposure or use and repeated cleanings because of the high degree of durability of the treated surface as can be obtained through the compositions of this invention.

To effect the treatment of a substrate, the fluorochemical silane, preferably in the form of an aqueous composition as disclosed above, is applied to the substrate. The amount of hydrolysable fluorochemical silane to be coated on the substrate will generally be that amount sufficient to produce a coating which is water and oil repellent, such a coating having at 20° C. a contact angle with distilled water of at least 80°, and a contact angle with n-hexadecane of at least 40°, measured after drying and curing of the coating. This coating can be extremely thin, e.g. 1 to 50 molecular layers, though in practice a useful coating may be thicker.

Preferably, the substrate should be clean prior to applying the compositions of the invention so as to obtain optimum characteristics, particularly durability. That is, the surface of the substrate to be coated should be substantially free of organic contamination prior to coating. Cleaning techniques depend on the type of substrate and include, for example, a solvent washing step with an organic solvent, such as acetone or ethanol. The coating composition is typically a relatively diluted aqueous composition, containing between 0.01 and 10 percent by weight of the fluorochemical silane, more preferably, between 0.03 and 3 percent by weight of the fluorochemical silane, and most preferably, between 0.1 and 2 percent by weight of the fluorochemical silane.

For ease of manufacturing and for reasons of costs, the compositions of the present invention will generally be prepared shortly before use by dispersing the fluorochemical silane of formula (I) in water. The composition should generally be free of acidic and basic substances to avoid premature hydrolysation of the hydrolysable water solubilising groups which could cause coagulation or settling out of the fluorochemical silane. A thus freshly prepared diluted solution will generally be stable for 1 or more days.

A wide variety of coating methods can be used to apply a composition of the present invention, such as brushing, spraying, dipping, rolling, spreading, and the like. A preferred coating method for application of a fluorochemical silane of the present invention includes spray application. Generally, the fluorochemical silane coating on the substrate will be subjected to heat. To effect heating, a substrate to be coated can typically be preheated at a temperature of for example between 60° C. and 150° C. This is of particular interest for industrial production, where eg. ceramic tiles can be treated immediately after the baking oven at the end of the production line. Alternatively, the substrate to be coated can be contacted with the treating composition at room temperature (typically, about 20° C. to about 25° C.) and subsequently dried at elevated temperature of e.g. 40° to 300° C. Following application, the treated substrate is typically polished with an acid or base solution to remove the hydrolyzable water solubilizing groups.

Although the inventor does not wish to be bound by this theory, compounds of the above mentioned formula I are believed to undergo reaction with the substrate surface to form a siloxane layer. For the preparation of a durable hydrophobic coating, an acid or a base catalyst should be present in order to cause hydrolysis of the water solubilizing silane end groups, and then condensation of the resulting silanol groups on and to the substrate. In this context, "siloxane" refers to —Si—O—Si— bonds to which are attached fluorochemical oligomer segments as given in formula I. A coating prepared from a coating composition that includes compounds of formula I can also include unreacted or uncondensed silanol groups.

To achieve good hydrophobicity and durability, organic or inorganic acid or base catalyst should be used. Organic acids include acetic acid, citric acid, formic acid, triflic acid, perfluorobutyric acid and the like. Examples of inorganic acids include sulphuric acid, hydrochloric acid and the like. Examples of useful amines include sodium hydroxide, potassium hydroxide and triethylamine. The acid or base catalyst will generally be applied to the coating after drying as a water based solution comprising between about 0.01 and 10%, more preferably between 0.05 and 5% by weight of the catalyst.

EXAMPLES

The following examples further illustrate the invention without the intention however to limit the invention thereto. All parts are by weight unless indicated otherwise.
Abbreviations AcA: acetic acid, available from Aldrich
CW 550: Carbowax™ 550, methoxy polyethyleneglycol with average molecular weight 550, available from Aldrich
CW 350: Carbowax™ 350, methoxy polyethyleneglycol with average molecular weight 350, available from Aldrich
MeFOSEA: N-methyl perfluorooctyl sulfonamido ethylacrylate
MeFBSEA: N-methyl perfluorobutyl sulfonamido ethylacrylate
A-174: $CH_2=C(CH_3)C(O)O(CH_2)_3Si(OCH_3)_3$, available from Aldrich
A-160: $HS(CH_2)_3Si(OCH_3)_3$, available from Aldrich
TEG: $HOCH_2CH_2OCH_2CH_2OCH_2CH_2OCH_3$, available from Aldrich
Dynasylan™ 8800: waterbased fluorochemical, available from Degussa-Hüls
FC-759: waterbased fluorochemical, available from 3M
FC-405: solvent based fluorochemical, available from 3M Methods of Application and Testing
Coating Method
In a first step, the substrates were cleaned and degreased with acetone. After cleaning, the substrates were preheated to 150° C. 1% aqueous mixtures of fluorochemical silanes as given in the respective examples were applied onto the hot substrates, by spray application at about 20 ml/minute.

After drying, the substrates were treated with a 3% solution of acetic acid in water. During this cleaning step, the initial hydrophilic coating transformed into a hydrophobic coating. The substrates were dried and cured at 150° C. during 15 minutes.
Contact Angles
The treated substrates were tested for their contact angles versus water (W) and n-hexadecane (0) using an Olympus TGHM goniometer. The contact angles were measured before (initial) and directly after abrasion (abrasion), unless otherwise indicated. The values are the mean values of 4 measurements and are reported in degrees. The minimum measurable value for a contact angle was 20. A value <20 meant that the liquid spread on the surface.
Abrasion Test
The treated substrates were abraded using an Erichsen cleaning machine, 3M High Performance Cloth (available from 3M) and CIF cleaner (available from Lever), using 40 cycles.
Synthesis of Fluorochemical Silanes (FCSIL)
Several fluorochemical silanes as given in table 1 were prepared similar to the 2 step synthesis of MeFOSEA/A-174/A-160/CW550 (molar ratio: 2/2/1/13.5) (FCSIL1): In a first step, a fluorochemical oligomer MeFOSEA/A-174/A-160 2/2/1 was prepared.

In a three-necked flask of 500 ml, fitted with a condenser, stirrer and thermometer, were placed 36.7 g (0.06 mol) MeFOSEA, 14.9 g (0.06 mol) A-174, 7.8 g (0.03 mol) A-160, 130 g ethylacetate and 0.1 g ABIN.

The mixture was degassed three times using aspirator vacuum and nitrogen pressure. The mixture was reacted under nitrogen at 75° C. during 8 hours. An additional 0.05 g ABIN was added and the reaction was continued for another 16 hrs at 75° C.; another 0.05 g ABIN was added and reaction continued at 82° C. for 2 hrs. A clear solution of the oligomeric fluorochemical silane MeFOSEA/A-174/A-160 in a molar ratio 2/2/1 was obtained.

In a second step, 220 g (0.4 moles) Carbowax™ 550 and 20 g heptane were added. The alkoxide exchange reaction was done at a temperature of 100–180° C. for 6 hrs, while stripping off solvent and exchanged ethanol. A brown, clear solution was obtained which upon cooling became solid. A 1% dispersion in water was made by vigorous stirring for 15 minutes at 40° C.

Further examples were prepared using above procedure, using molar ratios of reactants as indicated in table 1. Comparative fluorochemical silanes C-FCSIL 1-3 were prepared according to U.S. Pat. No. 5,274,159, example 2.

TABLE 1

Composition of Fluorochemical Silanes

| FCSIL | Composition | Molar ratio |
|---|---|---|
| 1 | MeFOSEA/A-174/A-160/CW550 | 2/2/1/13.5 |
| 2 | MeFOSEA/A-174/A-160/CW550 | 1/4/1/22.5 |
| 3 | MeFOSEA/A-174/A-160/TEG | 1/4/1/22.5 |
| 4 | MeFOSEA/A-174/A-160/CW550 | 4/4/1/22.5 |
| 5 | MeFOSEA/A-174/octylmercaptane/TEG | 1/4/1/18 |
| 6 | MeFBSEA/A-160/CW350 | 4/1/4.5 |
| 7 | MeFBSEA/A-174/A-160/TEG | 1/4/1/22.5 |
| 8 | MeFBSEA/A-174/A-160/TEG | 2/2/1/13.5 |
| 9 | MeFBSEA/A-174/A-160/TEG | 4/4/1/22.5 |
| 10 | MeFBSEA/A-174/A-160/TEG | 6/3/1/18 |
| 11 | MeFBSEA/A-174/A-160/TEG | 10/10/1/50 |
| 12 | MeFBSEA/A-174/mercaptoethanol/TEG | 2/2/1/9 |
| 13 | MeFBSEA/A-174/mercaptoethanol/ isocyanatopropyltrimethoxysilane/TEG | 2/2/1/1/13.5 |
| C-FCSIL-1 | $C_8F_{17}SO_2N(Et)(CH_2)_3Si(TEG)_3$ | |
| C-FCSIL-2 | $C_8F_{17}SO_2N(Et)(CH_2)_3Si(CW550)_3$ | |
| C-FCSIL-3 | $C_4F_9SO_2N(Me)(CH_2)_3Si(TEG)_3$ | |

Examples 1 to 5 and Comparative Examples C-1 to C-5

In Examples 1 to 5, white glazed Katayha tiles (7.5 cm×7.5 cm), were coated with 1% aqueous fluorochemical silane solutions as given in table 2, according to the general method. Comparative Examples C-1 and C-2 were made in the same way with comparative treating agents as given in table 2. Comparative Example C-3 was made with a solvent based (ethanol) fluorochemical treating agent FC-405. Comparative Examples C-4 and C-5 were made with commercially available water based fluorochemical treating agents for ceramic and porous stone surfaces. Contact angles were measured before and after abrasion with an Erichsen cleaning machine. The results are given in Table 2.

TABLE 2

Contact angles of wall tiles treated with fluorochemical silanes

| | | Contact angles (°) | | | |
|---|---|---|---|---|---|
| Ex | Treating agent | Initial W | Initial O | After abrasion W | After abrasion O |
| 1 | FCSIL-1 | 110 | 68 | 80 | 52 |
| 2 | FCSIL-2 | 105 | 66 | 75 | 50 |
| 3 | FCSIL-3 | 111 | 69 | 85 | 50 |
| 4 | FCSIL-4 | 108 | 65 | 72 | 49 |
| 5 | FCSIL-5 | 114 | 67 | 76 | 51 |
| C-1 | C-FCSIL-1 | 100 | 62 | 66 | 38 |
| C-2 | C-FCSIL-2 | 80 | 47 | 60 | 40 |
| C-3 | FC-405 (applied at 2%, from ethanol) | 105 | 62 | 76 | 45 |
| C-4 | FC-759 (applied at 6%) | 75 | 55 | 45 | 35 |
| C-5 | Dynasylan ™ 8800 (applied at 6%) | 90 | 55 | 54 | 30 |

The results indicated that tiles with high oil and water repellency could be made by using fluorochemical silanes according to the invention. High contact angles were measured, initially, but especially also after abrasion, indicating that highly durable coatings were made. The performance of the treated tiles was superior compared to tiles treated with commercially available treating agents. As can be seen from the results of Examples 1 to 5 compared to C-1 and C-2, there was an advantage, especially in oil repellency, in using fluorochemical silane oligomers, compared to the fluorochemical compound. Account needs to be taken that a difference in contact angle with distilled water of 10° and a difference in contact angle with n-hexadecane of 5° is considered to be significant.

Examples 6 to 13 and Comparative Example C-6

In examples 6 to 13 and Comparative Example C-6, the same kind of experiment was repeated with fluorochemical silane compounds as given in Table 3. The compositions of the treating agents and the contact angles of Katayha tiles treated therewith are given in Table 3.

TABLE 3

Katayha Tiles Treated with Fluorochemical Silane Compounds

| | | Contact angles (°) | | | |
|---|---|---|---|---|---|
| Ex | Treating agent | Initial W | Initial O | After abrasion W | After abrasion O |
| 6 | FCSIL-6 | 97 | 64 | 60 | 32 |
| 7 | FCSIL-7 | 93 | 61 | 59 | 35 |
| 8 | FCSIL-8 | 97 | 57 | 55 | 29 |
| 9 | FCSIL-9 | 95 | 60 | 65 | 32 |
| 10 | FCSIL-10 | 102 | 60 | 58 | 35 |
| 11 | FCSIL-11 | 95 | 58 | 55 | 29 |
| 12 | FCSIL-12 | 85 | 55 | 60 | 33 |
| 13 | FCSIL-13 | 90 | 57 | 58 | 37 |
| C-6 | C-FCSIL-3 (applied at 5%) | 78 | 45 | 45 | 25 |

Also in these experiments, tiles with high oil and especially water repellency were obtained by using fluorochemical silanes according to the invention. High contact angles were measured, initially and also after abrasion, indicating that highly durable coatings were made. The fluorochemical oligomer silanes (applied at 1%) clearly showed higher performance than the fluorochemical silane compound (applied at 5%).

What is claimed is:

1. A water soluble or water dispersible fluorochemical silane represented by the general formula:

$$X\text{-}M^f_n M^h_m M^a_r\text{-}G \qquad (I)$$

wherein X represents the residue of an initiator or hydrogen;

$M^f$ represents units derived from one or more fluorinated monomers;

$M^h$ represents units derived from one or more non-fluorinated monomers;

$M^a$ represents units having a silyl group represented by the formula:

$$\begin{array}{c} Y^4 \\ | \\ -\!-\!Si\!-\!Y^5 \\ | \\ Y^6 \end{array} \qquad (II)$$

wherein each of $Y^4$, $Y^5$ and $Y^6$ independently represents an alkyl group, an aryl group or a hydrolyzable group;

G is a monovalent organic group including the residue of a chain transfer agent;

n represents a value of 1 to 100;

m represents a value of 0 to 100;

and r represents a value of 0 to 100;

and n+m+r is at least 2;

with the proviso that at least one of the following conditions is fulfilled: (a) G contains a silyl group of the formula:

$$\begin{array}{c} Y^1 \\ | \\ -\!-\!Si\!-\!Y^2 \\ | \\ Y^3 \end{array} \qquad (III)$$

wherein $Y^1$, $Y^2$ and $Y^3$ each independently represents an alkyl group, an aryl group or a hydrolyzable group and at least one of $Y^1$, $Y^2$ and $Y^3$ represents a hydrolyzable water solubilising group or (b) r is at least 1 and at least one of $Y^4$, $Y^5$ and $Y^6$ represents a hydrolyzable water solubilizing group.

2. A water soluble or water dispersible fluorochemical silane according to claim 1 wherein said hydrolyzable water solubilizing group is an ionic group or a non-ionic group including a polyoxyalkylene group having 2 or 3 carbon atoms.

3. A water soluble or water dispersible fluorochemical silane according to claim 1 wherein r is 0 and wherein at least one of $Y^1$, $Y^2$, and $Y^3$ represents a polyoxyalkylene group having 2 or 3 carbon atoms.

4. A water soluble or water dispersible fluorochemical silane according to claim 1 wherein r is an integer of 1 to 30 and wherein at least one of $Y^4$, $Y^5$, and $Y^6$ represents a polyoxyalkylene group having 2 or 3 carbon atoms.

5. A water soluble or water dispersible fluorochemical silane according to claim 1 wherein m<n.

6. A water soluble or water dispersible fluorochemical silane according to claim 1 wherein the fluorochemical silane according to formula (I) contains at least 20% by weight of water solubilizing groups.

7. A water soluble or water dispersible fluorochemical silane according to claim 1 wherein said unit $M^f$ is derived from an ethylenically unsaturated monomer corresponding to the formula:

$$R_f\text{-}Q\text{-}E^1$$

wherein $R^f$ represents a fluoroaliphatic group including at least 3 carbon atoms or a fluorinated polyether group, Q represents an organic divalent linking group and $E^1$ represents a free radical polymerizable group.

8. A water soluble or water dispersible fluorochemical silane according to claim 7 wherein $R_f$ represents $C_4F_9$—.

9. A water soluble or water dispersible fluorochemical silane according to claim 1 wherein said unit $M^a$ is derivable from a monomer represented by the formula:

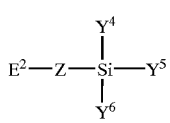

wherein $Y^4$, $Y^5$ and $Y^6$ have a meaning as defined in claim 1, Z represents an organic divalent linking group and $E^2$ represents a free radical polymerizable group.

10. A water soluble or water dispersible fluorochemical silane according to claim 1 wherein said water soluble or water dispersible fluorochemical silane has a water solubility or water dispersibility of at least 0.1% by weight.

11. An aqueous composition comprising a water soluble or water dispersible fluorochemical silane as defined in claim 1.

12. Method of treatment of a substrate comprising applying a water soluble or water dispersible fluorochemical silane as defined in claim 1 to a substrate.

13. Method according to claim 12 further comprising the step of heating to a temperature of 40° C. to 300° C.

14. Method according to claim 12 wherein said fluorochemical silane or an aqueous composition thereof is applied to said substrate in the presence of an acid or base catalyst or wherein subsequent to application of said fluorochemical silane or an aqueous composition thereof, an acid or base catalyst is applied.

15. Method according to claim 13 wherein said substrate is selected from the group consisting of ceramics, glass, stone, plastic and metal.

16. Treated substrate obtained by any of the method of claim 12.

17. Method of making a water soluble or water dispersible fluorochemical silane as defined in claim 1 comprising a free radical polymerization of fluorinated monomer and optionally a non-fluorinated monomer in the presence of a chain transfer agent wherein at least said chain transfer agent contains a silyl group represented by the formula:

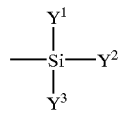

wherein $Y^1$, $Y^2$ and $Y^3$ each independently represents an alkyl group, an aryl group or a hydrolyzable group and at least one of $Y^1$, $Y^2$ and $Y^3$ represents a hydrolyzable water solubilising group;

and/or wherein said free radical polymerization involves copolymerization with a monomer having a silyl group represented by formula:

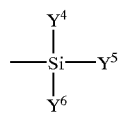

wherein each of $Y^4$, $Y^5$ and $Y^6$ independently represents an alkyl group, an aryl group or a hydrolyzable group and at least one of $Y^4$, $Y^5$ and $Y^6$ represents a hydrolyzable water solubilising group.

18. A method for making a water soluble or water dispersible fluorochemical silane as defined in claim 1 comprising preparation of a fluorochemical oligomer by free radical polymerization of a fluorinated monomer, optionally a non-fluorinated monomer in the presence of a chain transfer agent and at least said chain transfer agent contains a silyl group represented by the formula:

(A)

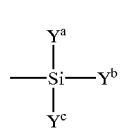

wherein $Y^a$, $Y^b$ and $Y^c$ each independently represents an alkyl group, an aryl group and at least one of $Y^a$, $Y^b$ and $Y^c$ represents a hydrolyzable group selected from an alkoxy group, an acyloxy group, an acyl group, an aryloxy group and a halogen;

and/or wherein said free radical polymerization involves copolymerization with a monomer having a silyl group represented by the above formula (A);

and wherein the thus obtained fluorochemical oligomer is further reacted with a compound containing water solubilising groups and which compound is capable of displacing one or more of the hydrolysable groups in the silyl moiety according to formula (A) above so as to introduce into said silyl moiety one or more hydrolysable water solubilising groups.

19. A method for making a water soluble or water dispersible fluorochemical silane as defined in claim 1 comprising (a) preparation of a fluorochemical oligomer by free radical polymerization of a fluorinated monomer and optionally a non-fluorinated monomer in the presence of a chain transfer agent and said chain transfer agent and/or a comonomer having a functional group available for further reaction after said free radical polymerization and being selected from the group consisting of a hydroxy group and an amino group (b) reacting a thus prepared fluorochemical oligomer with a compound according to the formula

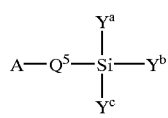

(B)

wherein A represents a functional group capable of undergoing a condensation reaction with said functional group of said comonomer or said functional group of said chain transfer agent, $Q^5$ represents an organic divalent linking group, $Y^a$, $Y^b$ and $Y^c$ each independently represents an alkyl group or an aryl group and at least one of $Y^a$, $Y^b$ and $Y^c$ represents a hydrolysable group selected from the group consisting of halogen, an alkoxy group, an acyloxy group, an acyl group and an aryloxy group; and (c) further reacting the thus obtained product with a compound containing water solubilising groups and which compound is capable of displacing one or more of the hydrolysable groups in the silyl moiety according to formula (B) above so as to introduce into said silyl moiety one or more hydrolysable water solubilising groups.

20. Method according to claim 18 wherein said compound containing water solubilising groups is a polyalkyleneoxide compound having a hydroxy or amino group.

21. A method according to claim 20 wherein said polyalkyleneoxide compound is a hydroxy or amino terminated $C_1$–$C_4$ alkyl ether of a polymer of ethylene oxide and/or propylene oxide.

22. A method according to claim 20 wherein said polyalkyleneoxide compound is a $C_1$–$C_4$ alkoxy polyalkyleneglycol wherein the alkylene of the polyalkylene glycol has 2 or 3 carbon atoms.

* * * * *

UNITED STATES PATENT AND TRADEMARK OFFICE
CERTIFICATE OF CORRECTION

PATENT NO.       : 6,977,307 B2
APPLICATION NO.  : 10/053001
DATED            : December 20, 2005
INVENTOR(S)      : Rudolf J. Dams It is certified that error appears in the above-identified patent and that said Letters Patent is hereby corrected as shown below:

Column 2
Line 38, delete "n represents a value of 1 to 100;" and insert --m represents a value of 0 to 100;--, therefor.

Column 4
Line 41, delete "$R^f$" and insert --$R_f$--, therefor.

Column 5
Line 23, delete "proximate" and insert --approximate--, therefor.

Column 6
Line 34, delete " $CF_3(CF_2)_7(CH_2)OCOCH=CH_2$" and insert
--$\mathbf{CF_3(CF_2)_7(CH_2)_2OCOCH=CH_2}$ --, therefor.

Column 7
Line 48, delete "vinylcloride" and insert --vinylchloride--, therefor.

Column 8
Line 35, after "VII" insert --:--.

Column 10
Line 2, after "VIII" delete "." and insert --:--, therefor.

Column 14
Line 57, delete "eg." and insert --e.g.,--, therefor.

Column 19
Line 28, claim 7, delete "$R^f$" and insert --$R_f$--, therefor.

Column 20
Line 1, claim 16, after "obtained by" delete "any of".

UNITED STATES PATENT AND TRADEMARK OFFICE
CERTIFICATE OF CORRECTION

PATENT NO. : 6,977,307 B2
APPLICATION NO. : 10/053001
DATED : December 20, 2005
INVENTOR(S) : Rudolf J. Dams It is certified that error appears in the above-identified patent and that said Letters Patent is hereby corrected as shown below:

Column 21,
Line 6, claim 19, after "formula" insert --:--.

Signed and Sealed this

Twenty-fourth Day of April, 2007

JON W. DUDAS
*Director of the United States Patent and Trademark Office*